(12) United States Patent
Maclaskey et al.

(10) Patent No.: US 9,741,219 B1
(45) Date of Patent: *Aug. 22, 2017

(54) TAMPER-PROOF BUILDING ALARM SYSTEM

(71) Applicants: Charles William Maclaskey, Gridley, KS (US); Clara Evelyn Maclaskey, Gridley, KS (US)

(72) Inventors: Charles William Maclaskey, Gridley, KS (US); Clara Evelyn Maclaskey, Gridley, KS (US)

( * ) Notice: Subject to any disclaimer, the term of this patent is extended or adjusted under 35 U.S.C. 154(b) by 60 days.

This patent is subject to a terminal disclaimer.

(21) Appl. No.: 15/338,635

(22) Filed: Oct. 31, 2016

Related U.S. Application Data

(62) Division of application No. 15/218,426, filed on Jul. 25, 2016, now Pat. No. 9,514,622.

(51) Int. Cl.
*G08B 13/08* (2006.01)

(52) U.S. Cl.
CPC .................... *G08B 13/08* (2013.01)

(58) Field of Classification Search
CPC .................. G06Q 10/00; A61B 1/00
See application file for complete search history.

(56) References Cited

U.S. PATENT DOCUMENTS

| | | | |
|---|---|---|---|
| 2009/0140858 A1* | 6/2009 | Gore | G08B 13/04 340/547 |
| 2014/0245798 A1* | 9/2014 | Beckman | E05B 19/00 70/14 |

* cited by examiner

*Primary Examiner* — Shirley Lu
(74) *Attorney, Agent, or Firm* — Donna Denise Mashburn Chapman; Mashburn Law Office, LLC

(57) ABSTRACT

A tamper-proof building alarm system comprising a number of sensing devices for sensing when a building entry point has been opened and an alarm unit comprising a tamper-proof housing and an alarm assembly. The tamper-proof housing includes a mounting base and a cover. The cover at least partially encloses the housing and prevents lateral access to the alarm assembly. The tamper-proof housing may include a locking system such that only authorized users have access to the alarm assembly.

20 Claims, 7 Drawing Sheets

TAMPER-PROOF BUILDING ALARM SYSTEM

RELATED APPLICATION

This application, which discloses and claims only subject matter disclosed in prior application Ser. No. 15/218,426, filed on Jul. 25, 2016, and entitled "TAMPER-PROOF BUILDING ALARM SYSTEM," claims only subject matter directed to an invention that is independent and distinct from that claimed in the prior application, and names the inventor or at least one joint inventor named in the prior application. Accordingly, this application may constitute a divisional application under 37 C.F.R. 1.53(b). The '426 application is hereby incorporated by reference in its entirety.

FIELD OF INVENTION

Embodiments of the present invention relate to building alarm systems that function to sound an audible alarm signal and/or emit an optical alarm signal when a building entry point such as a door or window is opened.

BACKGROUND

Alarm system tampering is a common problem in commercial buildings and rental properties. Typically, these devices can be disarmed by tampering with the alarm system itself. For example, building alarm systems can be disabled by severing or disconnecting an alarm wire, disconnecting the alarm from a power source, or placing tape and other objects over the alarm signal to reduce or eliminate the sound or light.

BRIEF SUMMARY

An improved tamper-proof building alarm system that overcomes the above tampering problems is provided.

A first embodiment of the invention is a tamper-proof building alarm system broadly comprising a number of sensing devices and an alarm unit. The sensing devices include a sensor for sensing whether a building entry point is open and a transmitter for transmitting a signal to the alarm unit indicating that the building entry point is open. The alarm unit includes a housing and an alarm assembly. The housing includes a mounting base for mounting electronic components thereto and a cover for preventing unauthorized access to the alarm assembly. The cover may include outer walls for preventing lateral access to the alarm assembly. The cover and the mounting base may form a gap therebetween for allowing alerts to emanate through the gap. The cover prevents access to the alarm assembly mounted in the housing.

The alarm assembly includes a receiver for receiving the signal from the sensing device, a controller, and an alarm output for generating an alert when the receiver receives the signal. The alarm may alert a user that the building entry point is open or may ward off an intruder.

A second embodiment of the invention is an alarm assembly substantially similar to the alarm assembly described above except that the cover is hinged to the mounting base and the housing further includes a locking mechanism having a magnetic locking pin. The locking pin is configured to lock the cover in a closed position and be retrieved or shifted via a magnetic key so as to allow the cover to be opened. In this way, only an authorized user may access the alarm assembly.

A third embodiment of the invention is similar to the alarm assembly described above except that the locking mechanism includes a pin having an outwardly biased ball bearing. The pin is configured to lock the cover in a closed position and be retrieved or shifted via a key configured to engage the pin by the ball bearing so as to allow the cover to be opened. In this way, only an authorized user may access the alarm assembly.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

Figure 1:
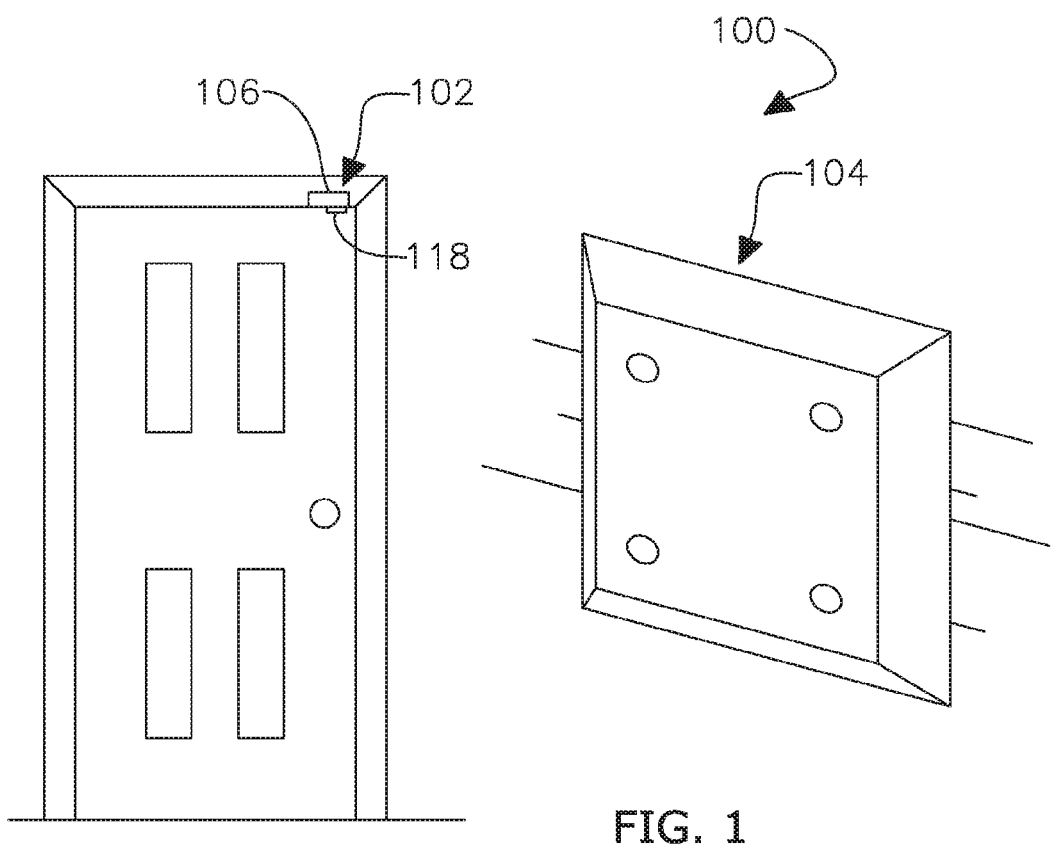
FIG. 1 is an overall view of a tamper-proof building alarm system constructed in accordance with an embodiment of the invention.
Figure 2:
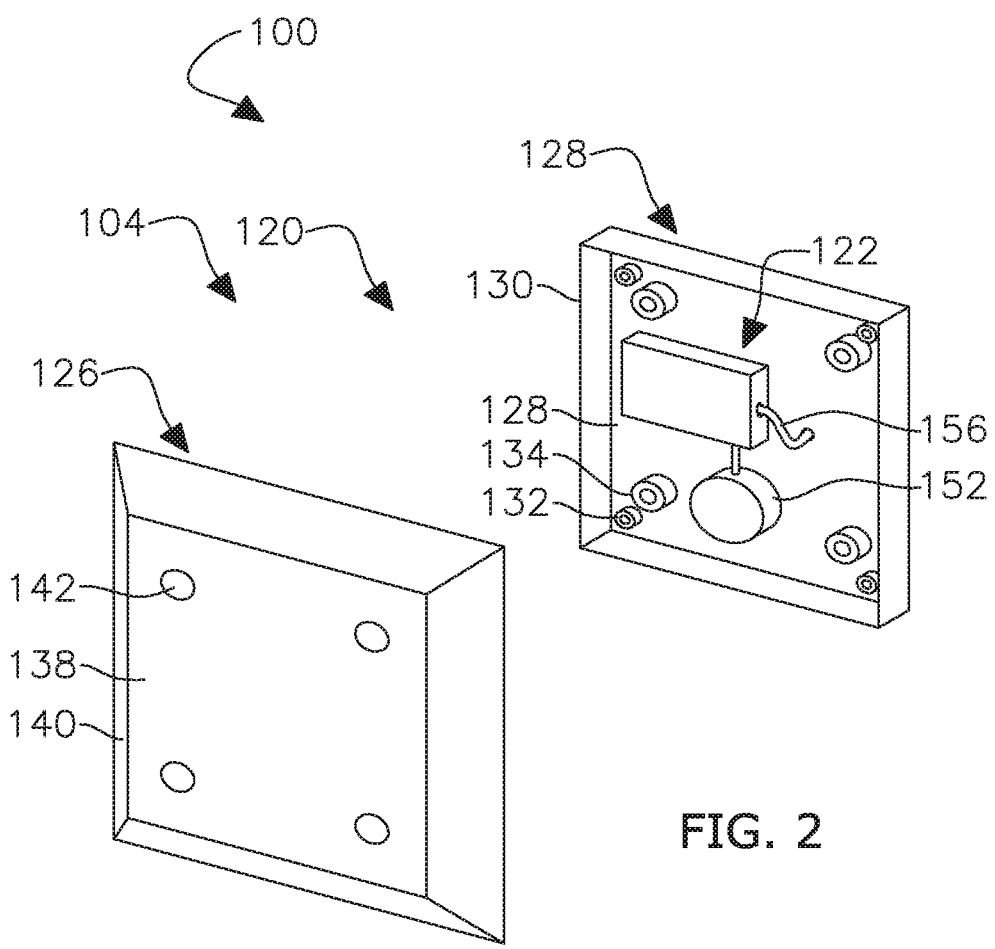
FIG. 2 is an exploded view of an alarm unit of the alarm system of FIG. 1.
Figure 3:
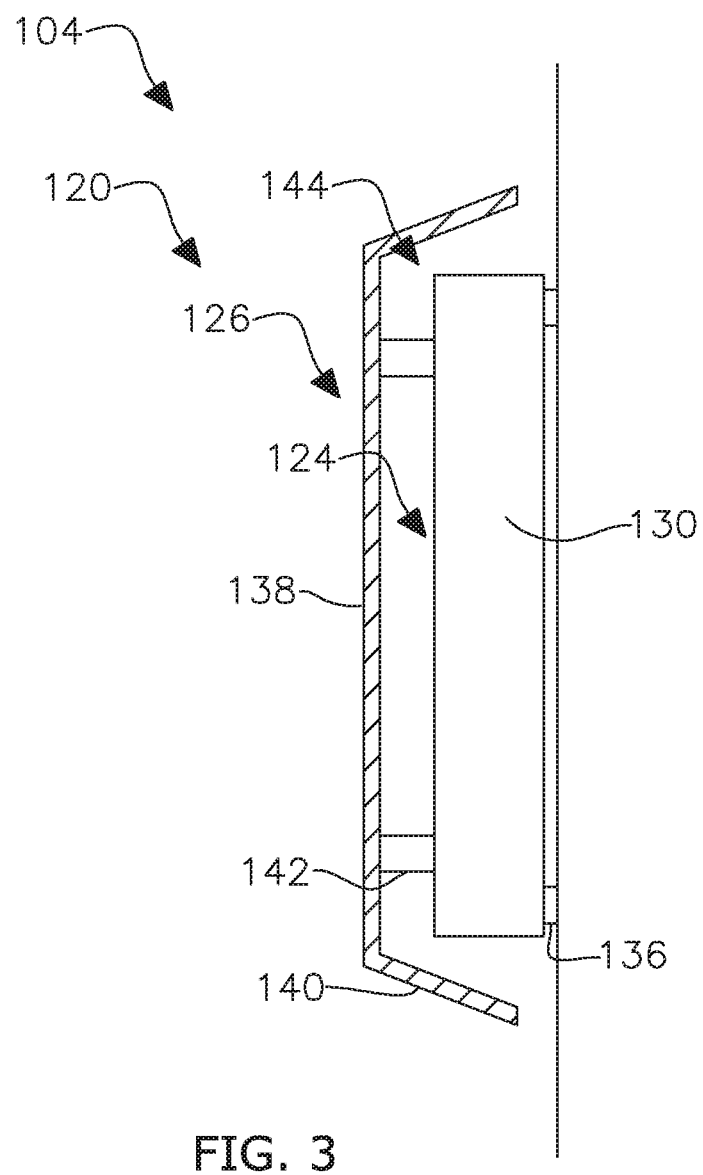
FIG. 3 is a side elevation cutaway view of the alarm unit of FIG. 2.
Figure 4:
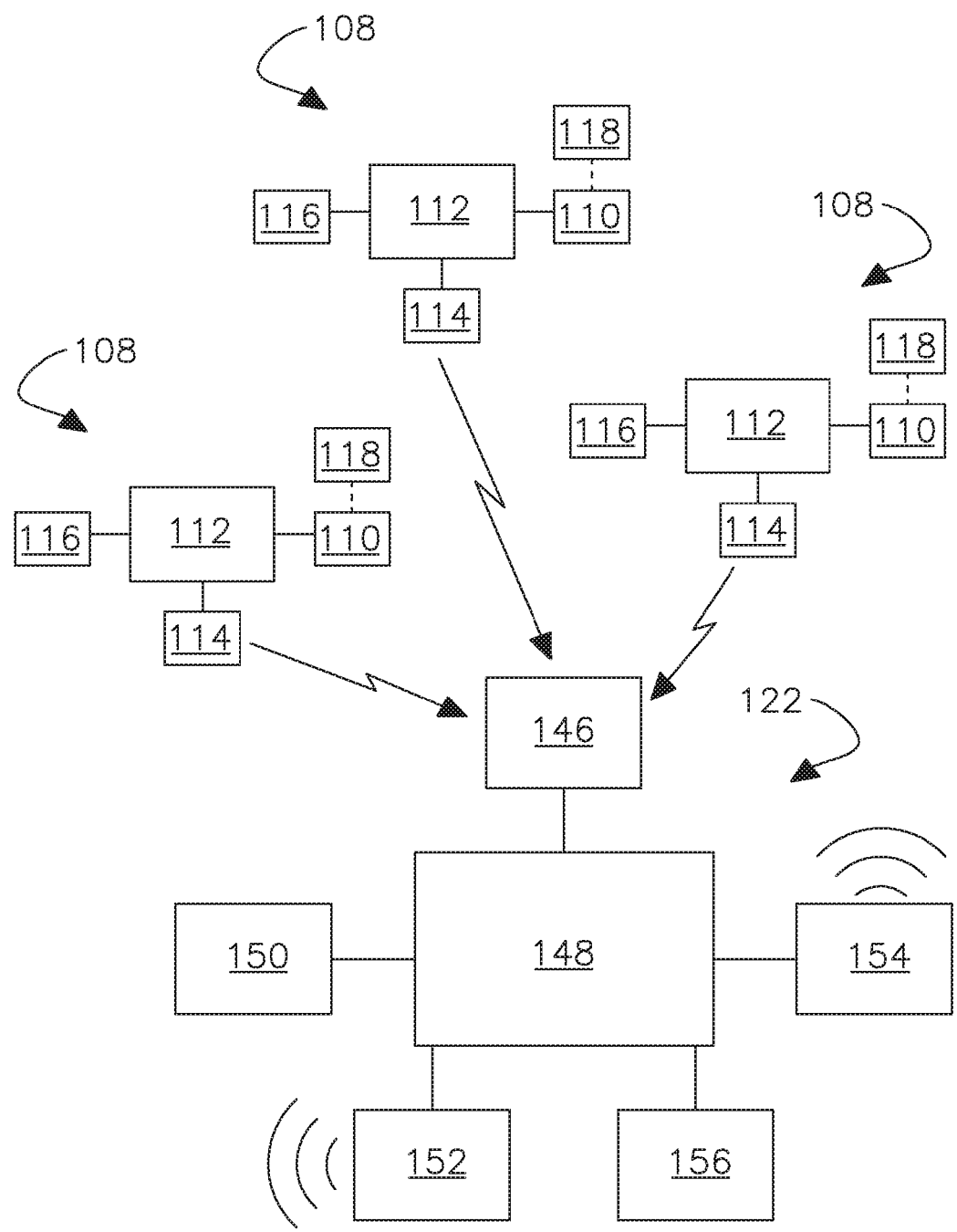
FIG. 4 is a schematic view of the alarm system of FIG. 1.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the current invention. The following detailed description is, therefore, not to be taken in a limiting sense. The scope of the current invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Turning to FIGS. 1-6, a tamper-proof building alarm system 100 constructed in accordance with an embodiment of the invention is illustrated. The tamper-proof building alarm system 100 broadly comprises a number of sensing devices 102 and an alarm unit 104.

The sensing devices 102 transmit a signal to the alarm unit 104 when a building entry point has been opened and each broadly comprise a sensor casing 106, and a sensor assembly 108. The sensor casing 106 houses some or all of the components of the sensor assembly 108 (described below) and may be formed of plastic, metal, or any other suitable durable material.

The sensor assembly 108 broadly comprises a sensor 110, a controller 112, a transmitter 114, a power source 116, and a trip element 118. The sensor 110 senses whether the trip element 118 is in a closed or non-tripped position and may be a magnetic sensor, proximity sensor, position sensor, NFC (near field communication) sensor, switch, or any other suitable sensor. The controller 112 receives the signal from the sensor 110 and instructs the transmitter 114 to transmit another signal to the alarm unit 104 indicating that the sensor has been tripped and may be a simple circuit, processor, or other controller. The transmitter 114 transmits the trip signal to the alarm unit 104 and may be an RF transmitter, NFC transmitter, Bluetooth transmitter, or other secure transmitter. In one embodiment, the transmitter 114 uses RF frequencies of between 100 KHz and 1,000 GHz with a range of at least 150 feet. The power source 116 powers the sensor assembly 108 and may be a battery, solar power unit, wall plug, or other power source. The trip element 118 is mounted to a movable part of the entry point such as a door, window, or garage door, and is movable between a closed or non-tripped position in which the trip element 118 is near or engaging the sensor 110 and an open or tripped position in which the trip element 118 is not near or not engaging the sensor 110. The trip element 118 may be a magnet, a block or wedge (for tripping a switch or proximity sensor), an NFC element, or any other suitable trip element. It will be understood that the trip element 118 may be mounted to a fixed structure such as a door jamb while the sensor casing 106 is mounted to a moving structure such as a door or window. In one embodiment, the sensing devices 102 may be Insteon® Hidden Door Sensors. In another embodiment, the sensing devices 102 do not include a trip element 118 and instead the sensor 110 is a biased mechanical member that is urged into a closed or engaged position when the door or window is closed and is biased to an open or un-engaged position when the door or window is open. An example of such an arrangement is the Insteon® Hidden Door Sensor.

The alarm unit 104 alerts an operator or homeowner that a sensor 110 of one of the sensor assemblies 104 has been tripped and broadly comprises a housing 120 and an alarm assembly 122. The alarm unit 104 may also actively monitor the statuses of the sensor assemblies 104.

The housing 120 is tamper proof for preventing unauthorized access to the alarm assembly 122 and broadly comprises a mounting base 124 and a cover 126. The mounting base 124 includes a back wall 128 and a number of side walls 130. The back wall 128 may include a number of mounting base mounting elements 132, cover mounting elements 134, and one or more openings for receiving a power cord, power outlet, circuit cords, and the like therethrough. The mounting base mounting elements 132 allow the housing 120 to be mounted to a wall, over a wall power outlet, or other desired mounting point and may include fastener openings for receiving mounting fasteners therethrough and a number of spacers 136 for spacing the housing 120 from the mounting point. The side walls 130 extend forwards from edges of the back wall 128 so as to prevent lateral access to the alarm assembly 122. It will be understood that the side walls 130 may instead be partially or completely integrated with the cover 126. The mounting base 124 may be formed of plastic, metal, composite, or any other suitable material.

The cover 126 encloses the alarm assembly 122 in the housing 120 and broadly includes a front wall 138 and a number of outer walls 140. The front wall 138 faces forward and may be relatively featureless so as not to attract attention. The front wall 138 may however include open-ended fastener chambers 142 extending rearward and configured to align with the cover mounting elements 134 for receiving fasteners therethrough. The open-ended fastener chambers 142 may be elongated such that the fasteners are less visible and more difficult to access. The fastener chambers 142 may be reinforced with crossbeams, ribs, or the like. The outer walls 140 extend rearward from the front wall 138 for preventing lateral access to the alarm assembly 122. In one embodiment, the outer walls 140 extend diagonally rearward and may be shaped so as to form a gap 144 between the outer walls 140 and the side walls 130 of the mounting base 124. The gap 144 may also extend between the front wall 138 and the distal ends of the side walls 130 of the mounting base 124 so that alarm sound or light can travel through the gap 144. The gap 144 is also small and does not have a direct "line of sight" to prevent access to the alarm assembly 122. The cover 126 may be formed of metal, plastic, composite, or any other suitable waterproof or weather resistant material.

The alarm assembly 122 is the central control of the tamper proof building alarm system 100 and broadly includes a receiver 146, a controller 148, a delay timer 150, an alarm output 152, a transmitter 154, and a power source 156. It will be understood that the alarm assembly 122 may include additional components or other equivalent components for providing central control to the alarm system 100.

The receiver 146 receives the trip signal transmitted by the transmitter 114 of one of the sensing devices 102 and may be an RF receiver, NFC receiver, Bluetooth receiver, or other secure receiver. The receiver 146 may be integrated with the transmitter 154 (i.e., a transceiver).

The controller 148 interprets or reacts to the trip signal, activates the delay timer 150, and instructs the alarm output 152 to generate an alert when a delay interval has expired. The controller 148 may be a simple circuit, processor, computing device, or combination thereof. The controller 148 may also include a memory and/or other computing components for logging alarm data and managing the alarm system 100. In one embodiment, the controller 148 is an Insteon® On/Off Outlet or an Insteon® On/Off Module.

The delay timer 150 begins a delay interval when the controller 148 receives a trip signal for delaying activation of the alarm output 152. The delay timer 150 may be set to any desired interval value such as one second to sixty minutes. This provides a user an amount of time to reset the alarm system if the building entry point is opened by an authorized entrant. The delay timer 150 may also be bypassed or omitted such that the alarm output 152 is activated immediately after the controller 148 receives the trip signal.

The alarm output 152 generates an audible or visual alert such as a loud ring, siren sound, buzz, strobe effect, or colored light and may be a horn, siren, buzzer, light, a combination, or other alarm output 152. The alarm output 152 may be positioned such that the alert is highly audible or visible.

The transmitter 154 is optional and may transmit a signal to a remote server or a mobile computing device of an operator, homeowner, or other user for alerting the user that the alarm system 100 has been activated. The transmitter 154 may be an RF transmitter, NFC transmitter, Bluetooth transmitter, or other secure transmitter and may be integrated with the receiver 146 as described above.

The power source 156 powers the alarm unit 104 and may be a battery, solar power unit, wall plug, or other power source. The power source 156 may be plugged into a wall outlet or another electronic device.

Use of the alarm system 100 will now be described in more detail. First, the sensing devices 102 may be placed near entry points of the building being secured. For example, one of the sensing devices 102 may be placed near a door, another sensing device 102 may be placed near a window, and yet another sensing device 102 may be placed near a garage door. The alarm unit 104 may be mounted in a utility room or other centralized location and optionally connected to a power outlet.

If one of the entry points is opened or compromised, the corresponding trip element 118 will be moved from a closed or engaged position to an open or non-engaged position such that the corresponding sensor detects that the trip element 118 is no longer in the closed or engaged position. The controller 112 of the sensing device 102 will then instruct the transmitter 114 to transmit a signal to the controller of the alarm unit 104 that the sensing device 102 has been activated. The signal may include additional information such an entry point identity.

The receiver 146 of the alarm unit 104 will receive the signal and the controller 112 will then activate the delay timer 150. The delay timer 150 will run according to the set time delay interval. When the time delay interval has expired, the controller 112 will then instruct the alarm output 152 to generate an alert for notifying the user that the alarm system 100 has been activated. The controller 148 may also instruct the transmitter 154 to transmit a signal to a remote server or a mobile computing device of an operator, homeowner, or other user for alerting the user that the alarm system 100 has been activated.

Figure 5:
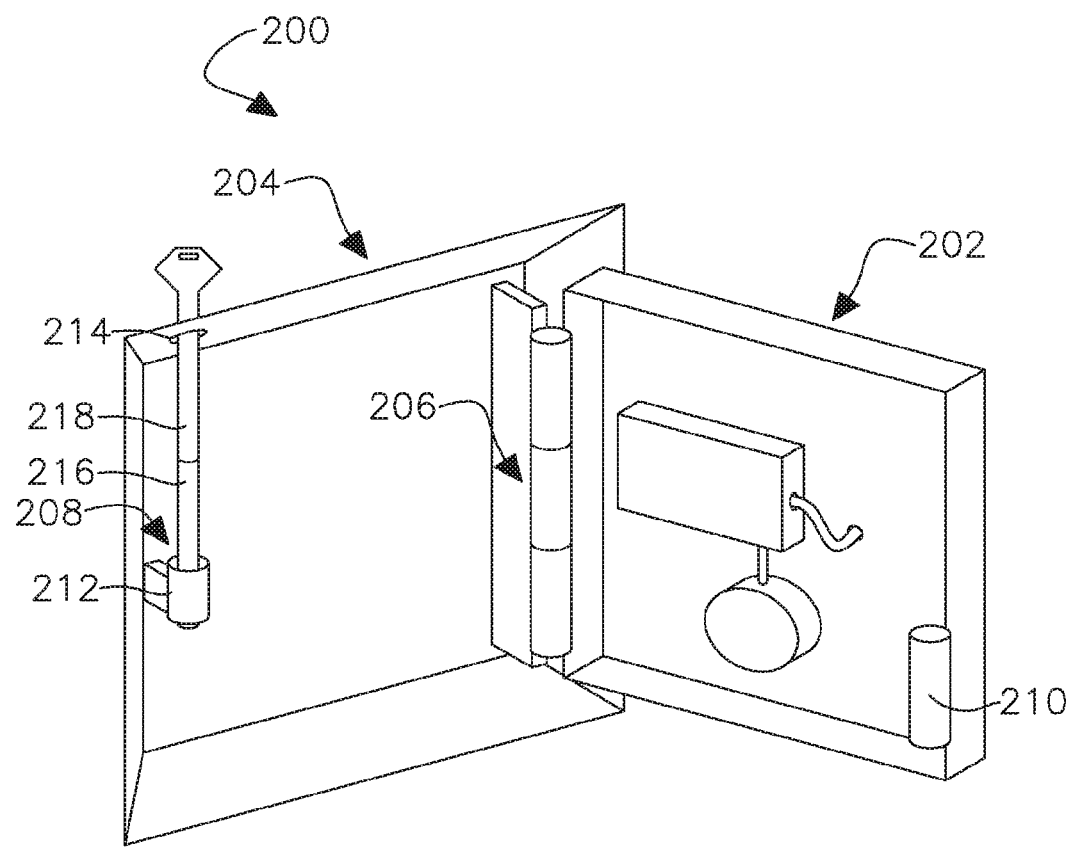
FIG. 5 is a perspective view of a tamper-proof building alarm system constructed in accordance with another embodiment of the invention.
Figure 6:
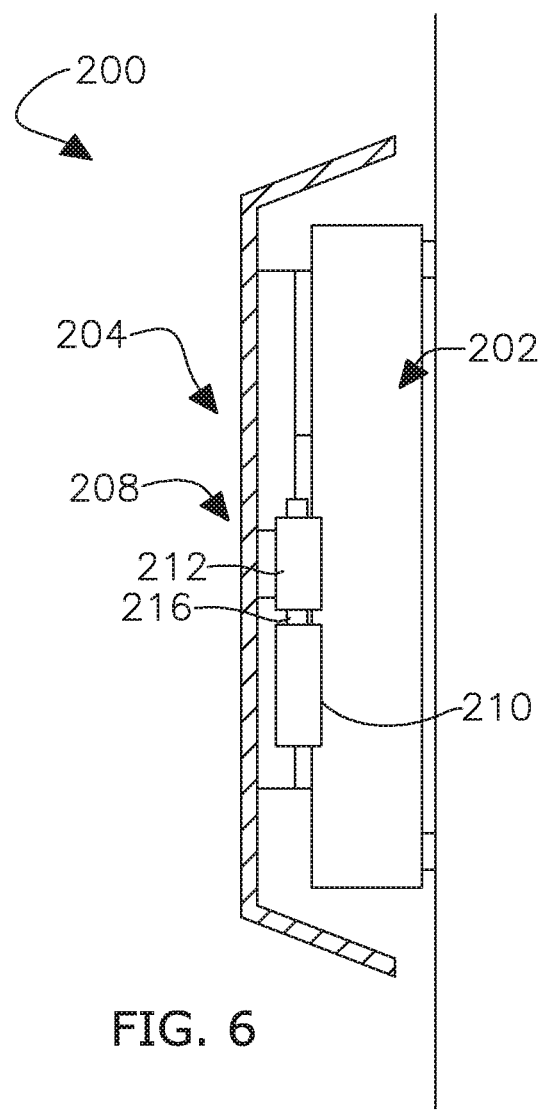
FIG. 6 is a side elevation cutaway view of the alarm system of FIG. 5.

Turning now to FIGS. 5 and 6, another embodiment of the invention is an alarm system 200 similar to the above described alarm system 100 except that the mounting base 202 and cover 204 are connected via a hinge 206 and cooperatively include a locking mechanism 208. The hinge 206 may be butterfly hinge, butt hinge, piano hinge, no-mortise hinge, or any other type of hinge.

The locking mechanism 208 ensures that only an authorized user can access the alarm system 100 and comprises a base pin catch 210, a cover pin guide 212, a key opening 214, a magnetic pin 216, and a magnetic key 218. The base pin catch 210 is fixed with the mounting base 202 and receives the magnetic pin 216 therein when the cover 204 is in the closed position. The base pin catch 210 may be an open-topped and closed-bottomed cylindrical tube or similar structure. The cover pin guide 212 guides the magnetic pin 216 vertically into and out of the base pin catch 210 and may be an open-topped and open-bottomed cylindrical tube fixed with the cover 204 and vertically positioned above and aligned with the base pin catch 210 when the cover 204 is in the closed position. The key opening 214 allows the magnetic key 218 to be inserted therethrough and is vertically positioned above and aligned with the cover pin guide 212. The magnetic pin 216 may be an elongated cylindrical configured to extend vertically at least between the base pin catch 210 and the cover pin guide 212. The magnetic key 218 may be an elongated open-ended cylindrical member configured to be inserted into the key opening 212 so as to magnetically attract and connect to the pin 216. The magnetic key 218 may then be pulled upwards through the key opening 214 so as to urge the magnetic pin 216 out of the base pin catch 210. The cover 204 may then be shifted to the open position when the magnetic pin 216 is clear of the base pin catch 210. In this way, only an authorized user in possession of the magnetic key 218 may open the alarm system 300.

Figure 7:
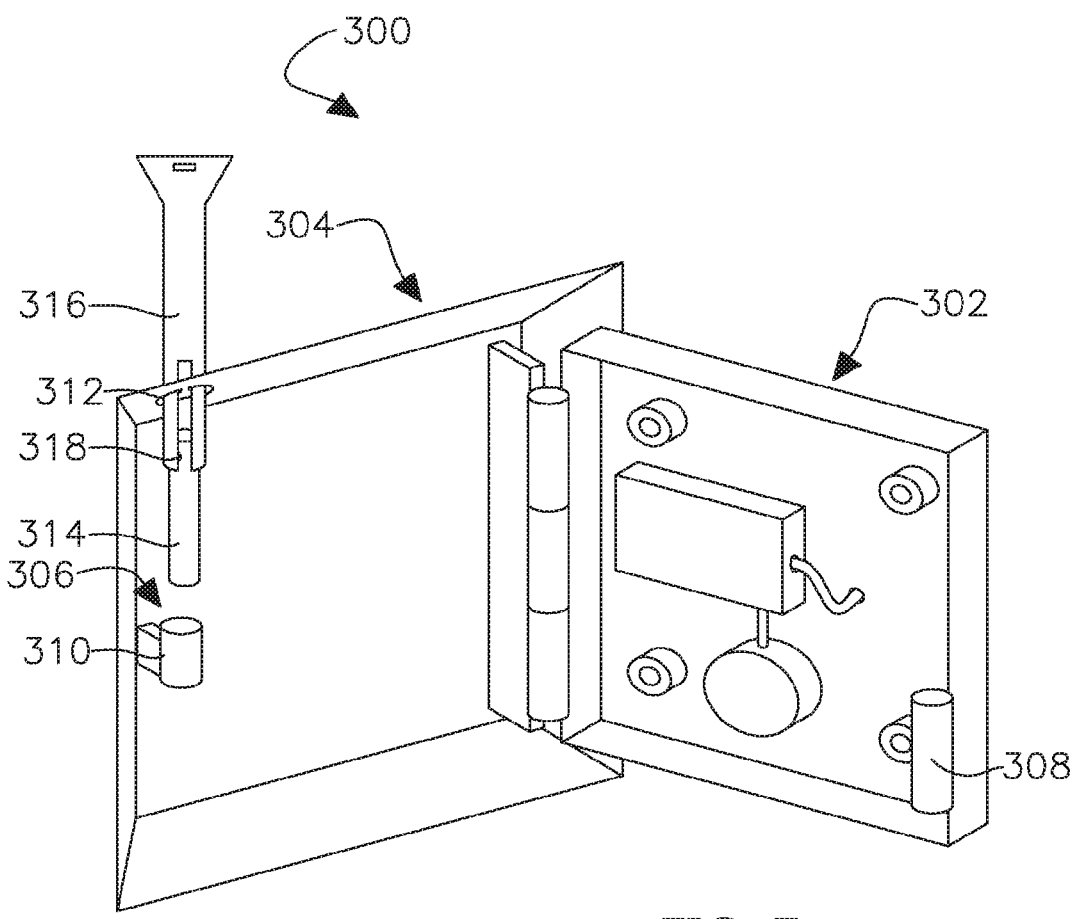
FIG. 7 is a perspective view of a tamper-proof building alarm system constructed in accordance with yet another embodiment of the invention.

Turning now to FIG. 7, yet another embodiment of the invention is an alarm system 300 similar to the above described alarm system 200 except that the mounting base 302 and cover 304 cooperatively include a locking mechanism 306 comprising a base pin catch 308, a cover pin guide 310, a key opening 212, a ball bearing pin 314, and a key 316. The base pin catch 308 is fixed with the mounting base 302 and receives the ball bearing pin 314 therein when the cover 304 is in the closed position. The base pin catch 308 may be an open-topped and closed-bottomed cylindrical tube or similar structure. The cover pin guide 310 guides the ball bearing pin 314 vertically into and out of the base pin catch 308 and may be an open-topped and open-bottomed cylindrical tube fixed with the cover 304 and vertically positioned above and aligned with the base pin catch 308 when the cover 304 is in the closed position. The key opening 212 allows the key 316 to be inserted therethrough and is vertically positioned above and aligned with the cover pin guide 310. The ball bearing pin 314 may be an elongated cylindrical configured to extend vertically at least between the base pin catch 308 and the cover pin guide 310. The ball bearing pin 314 may include a biased ball bearing 318 configured to engage the key 316 when the key 316 is inserted over the ball bearing pin 314. The key 316 may be an elongated open-ended cylindrical member configured to be inserted into the key opening 212 so as to engage the ball bearing pin 314 and catch on the biased ball bearing 318. The key 316 may then be pulled upwards through the key opening 212 so as to urge the ball bearing pin 314 out of the base pin catch 308. The cover 304 may then be shifted to the open position when the ball bearing pin 314 is clear of the base pin catch 308. In this way, only an authorized user in possession of the key 316 may open the alarm system 300.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A tamper-proof building alarm system comprising:
   a number of sensing devices each comprising:
      a sensor casing; and
      a sensor assembly at least partially housed in the sensor casing, the sensor assembly comprising:
         a sensor for sensing when a building entry point is open;

a sensor controller for controlling sensing device electronic components; and
a transmitter for transmitting a signal when the sensor senses that the building entry point is open;
an alarm unit comprising:
a housing comprising:
a mounting base including a back wall for mounting electronic components thereto and a fixed base pin catch;
a cover including a front wall for preventing front access to the electronic components, a number of outer walls extending rearward from the front wall for preventing lateral access to the electronic components; and
a hinge configured to pivotably connect the cover to the mounting base;
an alarm assembly at least partially housed in the housing, the alarm assembly comprising:
a receiver for receiving the signal from the transmitter of the sensor assembly;
an alarm assembly controller for controlling electronic components of the alarm assembly; and
an alarm output for generating an alert when the controller determines that a building entry point is open according to the signal received by the receiver.

2. The tamper-proof building alarm system of claim 1, wherein the cover and mounting base form a gap therebetween for allowing the alert to emanate therethrough.

3. The tamper-proof building alarm system of claim 1, wherein the alarm output is configured to generate an audible alert.

4. The tamper-proof building alarm system of claim 1, wherein the alarm output is configured to generate a visible alert.

5. The tamper-proof building alarm system of claim 1, wherein the sensor is a biased mechanical switch.

6. The tamper-proof building alarm system of claim 1, wherein the sensor is an optical sensor.

7. The tamper-proof building alarm system of claim 1, wherein the sensor is a magnetic sensor.

8. The tamper-proof building alarm system of claim 1, wherein the mounting base further includes side walls for further preventing lateral access to the alarm assembly.

9. The tamper-proof building alarm system of claim 1, wherein the outer walls of the cover extend diagonally rearward.

10. The tamper-proof building alarm system of claim 1, wherein the alarm assembly further comprises a delay timer for delaying activation of the alarm output.

11. The tamper-proof building alarm system of claim 1, wherein the cover further includes a pin guide configured to be aligned with the base pin catch when the cover is in a closed position, and a key opening for receiving a magnetic key therein, the key opening being aligned with the pin guide.

12. The tamper-proof building alarm system of claim 11, wherein the housing further includes a locking mechanism for locking the cover in a closed position, the locking mechanism including a magnetic pin configured to lock the cover in the closed position when inserted into the base pin catch and pin guide and configured to be retrieved from the base pin catch via the magnetic key so as to allow the cover to be shifted to an open position.

13. A tamper-proof building alarm system comprising:
a number of sensing devices each comprising:
a sensor casing; and
a sensor assembly at least partially housed in the sensor casing, the sensor assembly comprising:
a sensor for sensing when a building entry point is open;
a sensor controller for controlling sensing device electronic components; and
a transmitter for transmitting a signal when the sensor senses that the building entry point is open;
an alarm unit comprising:
a housing comprising:
a mounting base including a back wall for mounting electronic components thereto and a fixed base pin catch;
a cover including a front wall for preventing front access to the electronic components, a number of outer walls extending rearward from the front wall for preventing lateral access to the electronic components, a pin guide configured to be aligned with the base pin catch when the cover is in a closed position, and a key opening for receiving a magnetic key therein, the key opening being aligned with the pin guide;
a hinge configured to pivotably connect the cover to the mounting base; and
a locking mechanism for locking the cover in a closed position;
an alarm assembly at least partially housed in the housing, the alarm assembly comprising:
a receiver for receiving the signal from the transmitter of the sensor assembly;
an alarm assembly controller for controlling electronic components of the alarm assembly; and
an alarm output for generating an alert when the controller determines that a building entry is open according to the signal received by the receiver.

14. The tamper-proof building alarm system of claim 13, wherein the cover and mounting base form a gap therebetween for allowing the alert to emanate therethrough.

15. The tamper-proof building alarm system of claim 13, wherein the mounting base further includes side walls for further preventing lateral access to the alarm assembly.

16. The tamper-proof building alarm system of claim 13, wherein the outer walls of the cover extend diagonally rearward.

17. The tamper-proof building alarm system of claim 13, wherein the alarm output is configured to generate an audible alert.

18. The tamper-proof building alarm system of claim 13, wherein the alarm output is configured to generate a visible alert.

19. The tamper-proof building alarm system of claim 13, wherein the locking mechanism further includes a magnetic pin configured to lock the cover in the closed position when inserted into the base pin catch and pin guide and configured to be retrieved from the base pin catch via the magnetic key so as to allow the cover to be shifted to an open position.

20. A tamper-proof building alarm system comprising:
a number of sensing devices each comprising:
a sensor casing; and
a sensor assembly at least partially housed in the sensor casing, the sensor assembly comprising:
a sensor for sensing when a building entry point is open;
a sensor controller for controlling sensing device electronic components; and
a transmitter for transmitting a signal when the sensor senses that the building entry point is open;

an alarm unit comprising:
  a housing comprising:
    a mounting base including a back wall for mounting electronic components thereto and a fixed base pin catch;
    a cover including a front wall for preventing front access to the electronic components, a number of outer walls extending rearward from the front wall for preventing lateral access to the electronic components, a pin guide configured to be aligned with the base pin catch when the cover is in a closed position, and a key opening for receiving a magnetic key therein, the key opening being aligned with the pin guide;
    a hinge configured to pivotably connect the cover to the mounting base; and
    a locking mechanism for locking the cover in a closed position, the locking mechanism including a magnetic pin configured to lock the cover in the closed position when inserted into the base pin catch and pin guide and configured to be retrieved from the base pin catch via the magnetic key so as to allow the cover to be shifted to an open position;
  an alarm assembly at least partially housed in the housing, the alarm assembly comprising:
    a receiver for receiving the signal from the transmitter of the sensor assembly;
    an alarm assembly controller for controlling electronic components of the alarm assembly; and
    an alarm output for generating an alert when the controller determines that a building entry is open according to the signal received by the receiver.

* * * * *